(12) United States Patent
Shamay et al.

(10) Patent No.: US 11,109,913 B2
(45) Date of Patent: Sep. 7, 2021

(54) APPARATUS AND METHOD FOR NERVE ABLATION IN THE WALL OF THE GASTOINTESTINAL TRACT

(71) Applicant: DIGMA MEDICAL LTD., Petah Tikva (IL)

(72) Inventors: Yonatan Shamay, Tel Aviv-Jaffa (IL); Boaz Behar, Ganey Tikva (IL); Ilan Ben Oren, Modiin (IL)

(73) Assignee: DIGMA MEDICAL LTD., Petah Tikva (IL)

( * ) Notice: Subject to any disclaimer, the term of this patent is extended or adjusted under 35 U.S.C. 154(b) by 119 days.

(21) Appl. No.: 16/323,741

(22) PCT Filed: Aug. 14, 2017

(86) PCT No.: PCT/IL2017/050898
§ 371 (c)(1),
(2) Date: Feb. 6, 2019

(87) PCT Pub. No.: WO2018/033910
PCT Pub. Date: Feb. 22, 2018

(65) Prior Publication Data
US 2019/0167349 A1    Jun. 6, 2019

Related U.S. Application Data

(60) Provisional application No. 62/374,842, filed on Aug. 14, 2016.

(51) Int. Cl.
*A61B 18/18*    (2006.01)
*A61B 18/24*    (2006.01)
(Continued)

(52) U.S. Cl.
CPC ............ *A61B 18/24* (2013.01); *A61B 5/0086* (2013.01); *A61B 5/4255* (2013.01);
(Continued)

(58) Field of Classification Search
CPC ........... A61B 18/24; A61B 6/00; A61B 18/20; A61B 5/4836; A61B 5/0086;
(Continued)

(56) References Cited

U.S. PATENT DOCUMENTS

| 3,858,577 A | 1/1975 | Bass et al. |
| 5,029,574 A | 7/1991 | Shimamura et al. |

(Continued)

FOREIGN PATENT DOCUMENTS

| CN | 101400299 A | 4/2009 |
| EP | 0288576 | 11/1988 |

(Continued)

OTHER PUBLICATIONS

Cummings et al., (2004) Gastric bypass for obesity: mechanisms of weight loss and diabetes resolution. J Clin Endocrinol Metab 89(6): 2608-15.

(Continued)

*Primary Examiner* — Rex R Holmes
(74) *Attorney, Agent, or Firm* — The Roy Gross Law Firm, LLC; Roy Gross

(57) ABSTRACT

Catheter for real-time evaluation of duodenal ablation, the catheter including an expandable member configured to stretch the duodenal wall and to generate a fixed distance between a center of the catheter and the duodenal wall; a laser transmitting element coupled with the catheter body and configured to transmit a first laser beam and a second laser beam; wherein the first laser beam is configured to cause ablative damage in a region of the duodenal wall as a result of its impingement thereon, and wherein the second laser beam is configured to detect modifications in the region of the duodenal wall resulting from the impingement of the first laser beam thereon.

19 Claims, 8 Drawing Sheets

(51) Int. Cl.
  *A61B 6/00* (2006.01)
  *A61B 18/20* (2006.01)
  *A61B 5/00* (2006.01)
  *A61B 18/14* (2006.01)
  *A61B 17/00* (2006.01)
  *A61B 18/00* (2006.01)
  *A61B 18/22* (2006.01)

(52) U.S. Cl.
  CPC .......... *A61B 5/4836* (2013.01); *A61B 5/6853* (2013.01); *A61B 6/00* (2013.01); *A61B 18/14* (2013.01); *A61B 18/20* (2013.01); *A61B 18/22* (2013.01); *A61B 2017/00057* (2013.01); *A61B 2017/00128* (2013.01); *A61B 2018/0022* (2013.01); *A61B 2018/00494* (2013.01); *A61B 2018/00577* (2013.01); *A61B 2018/00642* (2013.01); *A61B 2018/00785* (2013.01); *A61B 2018/00904* (2013.01); *A61B 2562/0233* (2013.01)

(58) Field of Classification Search
  CPC ..... A61B 5/4255; A61B 5/6853; A61B 18/14; A61B 2018/00642; A61B 2562/0233; A61B 18/22; A61B 2018/0022; A61B 2017/00057; A61B 2017/00128; A61B 2018/00494; A61B 2018/00577; A61B 2018/00785; A61B 2018/00904
  See application file for complete search history.

(56) References Cited

U.S. PATENT DOCUMENTS

| | | |
|---|---|---|
| 5,693,043 A | 12/1997 | Kittrell et al. |
| 6,134,003 A | 10/2000 | Tearney et al. |
| 6,485,413 B1 | 11/2002 | Boppart et al. |
| 6,832,114 B1 | 12/2004 | Whitehurst et al. |
| 6,914,733 B2 | 7/2005 | Dong et al. |
| 7,096,070 B1 | 8/2006 | Jenkins et al. |
| 7,363,076 B2 | 4/2008 | Yun et al. |
| 7,430,450 B2 | 9/2008 | Imran |
| 7,494,661 B2 | 2/2009 | Sanders |
| 7,582,081 B2 | 9/2009 | Hofer et al. |
| 7,620,455 B2 | 11/2009 | Maschino |
| 7,835,074 B2 | 11/2010 | Jacobsen et al. |
| 8,095,218 B2 | 1/2012 | Gross et al. |
| 8,150,518 B2 | 4/2012 | Levin et al. |
| 8,340,760 B2 | 12/2012 | Dobak, III |
| 8,568,399 B2 | 10/2013 | Azamian et al. |
| 8,945,107 B2 | 2/2015 | Buckley et al. |
| 2002/0183622 A1 | 12/2002 | Zuluaga et al. |
| 2003/0144708 A1 | 7/2003 | Starkebaum |
| 2004/0082859 A1 | 4/2004 | Schaer |
| 2004/0172088 A1 | 9/2004 | Knudson et al. |
| 2004/0215180 A1 | 10/2004 | Starkebaum et al. |
| 2004/0248188 A1 | 12/2004 | Sanders |
| 2005/0183732 A1 | 8/2005 | Edwards |
| 2005/0251116 A1 | 11/2005 | Steinke et al. |
| 2006/0122584 A1 | 6/2006 | Bommannan et al. |
| 2007/0016262 A1 | 1/2007 | Gross et al. |
| 2007/0060906 A1 | 3/2007 | Wu |
| 2007/0081236 A1 | 4/2007 | Tearney et al. |
| 2007/0179487 A1* | 8/2007 | Tearney ............... A61B 5/0066 606/15 |
| 2008/0086180 A1 | 4/2008 | Ben-Ezra et al. |
| 2008/0275445 A1 | 11/2008 | Kelly et al. |
| 2009/0030473 A1 | 1/2009 | Khawaled et al. |
| 2009/0062881 A1 | 3/2009 | Gross et al. |
| 2009/0086213 A1 | 4/2009 | Masuda |
| 2009/0234417 A1 | 9/2009 | Pastena et al. |
| 2009/0253990 A1 | 10/2009 | Lieber et al. |
| 2010/0049188 A1 | 2/2010 | Nelson et al. |
| 2010/0114150 A1 | 5/2010 | Magal |
| 2010/0268297 A1 | 10/2010 | Neisz |
| 2010/0280504 A1 | 11/2010 | Manzke et al. |
| 2011/0130708 A1 | 6/2011 | Perry et al. |
| 2011/0208173 A1 | 8/2011 | Sobotka et al. |
| 2011/0208175 A1 | 8/2011 | Sobotka et al. |
| 2011/0257641 A1 | 10/2011 | Hastings et al. |
| 2012/0136417 A1 | 5/2012 | Buckley et al. |
| 2012/0179228 A1 | 7/2012 | Decharms |
| 2013/0178910 A1 | 7/2013 | Azamian et al. |
| 2013/0197555 A1 | 8/2013 | Schaer |
| 2013/0345670 A1 | 12/2013 | Rajagopalan et al. |
| 2014/0017635 A1 | 1/2014 | Fischer |
| 2014/0074077 A1 | 3/2014 | Lane |
| 2014/0088575 A1 | 3/2014 | Loeb |
| 2014/0088581 A1 | 3/2014 | Kelly et al. |
| 2014/0187619 A1 | 7/2014 | Pasricha et al. |
| 2015/0148738 A1 | 5/2015 | Caplan et al. |

FOREIGN PATENT DOCUMENTS

| | | | |
|---|---|---|---|
| EP | 1567082 | | 8/2005 |
| EP | 2548606 A1 | | 1/2013 |
| JP | 2009536531 A1 | | 10/2009 |
| JP | 2014508580 A | | 4/2014 |
| WO | 02/00172 | | 1/2002 |
| WO | 2004/069331 | | 8/2004 |
| WO | 2004/112883 | | 12/2004 |
| WO | 2007/007339 | | 1/2007 |
| WO | 2007149602 A2 | | 12/2007 |
| WO | 2007149603 A2 | | 12/2007 |
| WO | 2008/041233 | | 4/2008 |
| WO | 2008/137757 | | 11/2008 |
| WO | 2011/156736 | | 12/2011 |
| WO | 2012/099974 | | 7/2012 |
| WO | 2012099974 A2 | | 7/2012 |
| WO | 2012/122460 | | 9/2012 |
| WO | 2013/012892 | | 1/2013 |
| WO | 2013/082587 | | 6/2013 |
| WO | 2013/130655 | | 9/2013 |
| WO | 2013/159066 | | 10/2013 |
| WO | 2014/022436 | | 2/2014 |
| WO | 2014/026055 | | 2/2014 |
| WO | 2014/055997 | | 4/2014 |
| WO | 2014/118738 | | 8/2014 |
| WO | 2014/197632 | | 12/2014 |
| WO | 2015/159296 | | 10/2015 |
| WO | WO-2015159296 A1 * | 10/2015 | ............... A61B 6/00 |

OTHER PUBLICATIONS

Dougherty et al., (1998) Photodynamic therapy. J Natl Cancer Inst 90(12): 889-905.

Myslovich (2001) Stomach and duodenum ulcer: comparing the efficiency of three laser therapeutic techniques. Proc. SPIE 4422, Low-Level Laser Therapy, 74 (Apr. 26, 2001); doi:10.1117/12.425517.

Oraevsky et al., (1996) Plasma mediated ablation of biological tissues with nanosecond-to-femtosecond laser pulses: relative role of linear and nonlinear absorption. IEEE Journal of Selected Topics in Quantum Electronics 2(4): 801-809.

Portes and Albrecht (2001) Etiology of type II diabetes mellitus: role of the foregut. World J Surg 25(4): 527-31.

Rubino and Gagner (2002) Potential of surgery for curing type 2 diabetes mellitus. Ann Surg 236(5): 554-9.

Rubino et al., (2004) The early effect of the Roux-en-Y gastric bypass on hormones involved in body weight regulation and glucose metabolism. Ann Surg 240(2): 236-42.

Rubino et al., (2006) The mechanism of diabetes control after gastrointestinal bypass surgery reveals a role of the proximal small intestine in the pathophysiology of type 2 diabetes. Ann Surg 244(5): 741-9.

Verdam et al., (2012) An update on less invasive and endoscopic techniques mimicking the effect of bariatric surgery. J Obes 2012: 597871.

(56) References Cited

OTHER PUBLICATIONS

Wikipedia (2012) "Submucosa" (https://en.wikipedia.org/wiki/Submucosa), retrieved Dec. 26, 2019.

* cited by examiner

APPARATUS AND METHOD FOR NERVE ABLATION IN THE WALL OF THE GASTOINTESTINAL TRACT

RELATED APPLICATIONS

This application is a National Phase of PCT Patent Application No. PCT/IL2017/050898 having International filing date of Aug. 14, 2017 which claims the benefit of priority of U.S. Provisional Application No. 62/374,842 filed on Aug. 14, 2016. The contents of the above applications are all incorporated by reference as if fully set forth herein in their entirety.

TECHNICAL FIELD

The disclosure generally relates to an apparatus and method for providing feedback to nerve ablation in the wall of the gastrointestinal tract (GI).

BACKGROUND

Obesity is thought to be one of the primary causes of type 2 diabetes, especially in people who are genetically predisposed for the disease. Obesity is often treated by performing a bariatric surgery procedure (also known as weight-loss surgery) on the gastrointestinal tract of an obese patient in order to reduce weight. Multiple clinical studies and reports have indicated that in addition to weight-loss, certain bariatric surgery procedures can contribute to remission or improvement in disease management of type-2 diabetes, as well as to reduction in insulin resistance. This is specifically the case in certain bariatric procedures that bypass the proximal part of the gastrointestinal (GI) tract, such as Roux-en-Y gastric bypass (RYGB), duodenal-jejunal bypass (DJB) surgery and gastrojejunal bypass (GJB) surgery, all aimed at bypassing the duodenum. Unfortunately, bariatric surgery is associated with high risk and high cost and is not the optimal solution for management of the majority of T2D and non-obese patients, estimated at hundreds of millions worldwide. Consequently, bariatric surgery is typically not considered a disease management tool for the majority of T2D patients.

Attempts to gain effects similar to bariatric surgery include the use of minimally invasive devices, such as those inserted endoluminally, including staplers for reducing stomach size, intra-gastric balloons, implantation of electrical stimulators that intervene with stomach function (gastric electrical stimulation), sleeves that bypass the duodenum (e.g. EndoBarrier®, GI Dynamics™ and radio-frequency (RF) ablation applied to the surface of the organ with non-penetrating electrodes, which target duodenum mucosa, or by ablation of the area around the pyloric sphincter. However, these methods suffer from certain inherent limitations, such association with adverse events and unwarranted side effects (e.g. vomiting, nausea, abdominal pain, mucosal tear, bleeding, migration and obstruction), necessitating early device removal, complications, limited or even lack of efficacy.

Laser ablation has been suggested as a method for selectively blocking part of the neural activity in the small intestine, and preferably in the duodenum of a subject. However, generation of neural impairment within the wall of the intestine is challenging; because the wall is very thin, thickness is subject to high inter and intra patient variability, as well as folds and secretion elements. Injury or perforation of wall can be hazardous.

Accordingly, it is desired to provide a means to monitor, control and/or evaluate the efficiency of the ablation process during the procedure.

SUMMARY OF THE INVENTION

The present disclosure relates to methods, devices and systems for monitoring, controlling and/or evaluating the efficiency of the ablation process during the procedure.

Laser ablation has been suggested as an efficient procedure for selectively blocking neural activity in the small intestine, preferably in the duodenum of a subject. Without being bound by any theory, the ablation can impact neurohormonal and/or other signals triggered by food passing through the gastrointestinal (GI) tract, and thus the subject's sense of satiety.

However, neural impairment within the wall of the intestine is challenging, as the wall is very thin, folds and is subject to high inter and intra patient variability. At the same time, injury and/or perforation of the intestine wall can be hazardous.

Advantageously, the device, method and system, disclosed herein, enables monitoring and/or evaluating, in real-time, the extent of impact caused to the duodenal wall, and optionally to adjusting ablation parameters accordingly.

The device may advantageously include an expandable member, such as a non-compliant balloon, configured to stretch out the duodenal wall, thereby ensuring that the inner diameter of the duodenum will be essentially constant along the section covered by, stretched and/or associated with the balloon. This advantageously enables to ensure that a catheter inserted into the duodenum will be positioned in the center of the duodenum at the region designated for treatment, such that the circumferential ablation will be of an essentially same dose of laser energy, regardless of its orientation. The described mechanism for keeping the ablation element concentric in a "moving and dynamic" round organ such as the gut—can be done using a laser or any other non-direct energy emitting radiator—such as ultrasound or electromagnetic radiation. Most such methods have an effect on the tissue directly correlated with their linear velocity on the tissue rather than angular velocity, and are thus particularly beneficial for laser ablation.

The device further includes a laser transmitting element configured to transmit a first laser radiation to a target region of the duodenal wall, thereby causing ablation and/or modification thereof, and a second laser radiation configured to enabling scanning of the tissue region, thus obtaining a feedback indicative of the degree of impact caused to the tissue as a result of the first, ablative laser radiation impinging thereon. Advantageously, this enables real-time evaluation of modification in the treated tissue.

According to some embodiments, the second laser beam may be delayed relative to the first laser beam, with respect to an essentially same target region. This advantageously enables photo thermal and/or photo chemistry processes to happen prior to the monitoring by the feedback beam.

In addition, according to some embodiments, the spot diameter of the first, ablative radiation, may be smaller than the spot diameter of the second, evaluative radiation. This advantageously enables to evaluate a "collateral" effect caused to tissue not directly ablated, but affected due to its proximity to the directly ablated tissue.

According to some embodiments, there is provided a device for real-time evaluation of duodenal ablation, the device comprising a catheter comprising an expandable member configured to stretch the duodenal wall and to generate a fixed distance between a center of the catheter and the duodenal wall; a laser transmitting element coupled with the catheter body and configured to transmit a first laser beam and a second laser beam; wherein the first laser beam has a first wavelength and a first spot diameter and is configured to cause ablative damage in a region of the duodenal wall as a result of its impingement thereon, and wherein the second laser beam has a second wavelength and a second spot diameter and is configured to detect modifications in the region of the duodenal wall resulting from the impingement of the first laser beam thereon; and a deflective optical element functionally coupled with the laser emitting element and configured to direct the laser beam to a region on and/or beneath the duodenal wall.

According to some embodiments, the laser emitting element may include a first optical fiber configured to transmit the first laser beam and a second optical fiber configured to transmit the second laser beam. According to some embodiments, the first and second fibers are spatially off-set.

According to some embodiments, the laser transmitting element may further include a lens configured to deflect the first laser beam, such that the first and second laser beams are transmitted towards different target areas of the duodenal wall and/or such that the second laser beam impinges on a given target area at a delay relative to the impingement of the first laser beam on the same area, when the deflective optical elements are rotated.

According to some embodiments, the laser emitting element may include or be a double cladded fiber. According to some embodiments, the first laser beam is delivered through a core of the double cladded fiber, and the second beam is delivered through the clad of the double cladded fiber.

According to some embodiments, the laser transmitting element may further include a dispersive element configured to selectively refract the first and/or second laser beam, such that the first and second laser beams are transmitted towards different target areas of the duodenal wall and/or such that the second laser beam impinges on a given target area at a delay relative to the impingement of the first laser beam on that target area, when the deflective optical elements are rotated.

According to some embodiments, the first wavelength is 1550 nm or 1567 nm. According to some embodiments, the second wavelength is 980 nm.

According to some embodiments, the second spot diameter is larger than the first spot diameter, thereby enabling evaluation of ablative damage caused to tissue directly and indirectly affected by the first laser beam.

According to some embodiments, the device may further include a processing circuitry configured to evaluate the extent of impact on the region of the duodenal wall, based on the detected modifications therein.

According to some embodiments, there is provided a method for real-time evaluation of duodenal ablation, the method including: inserting a catheter into a duodenum of a subject; deploying an expandable member delivered by the catheter, thereby stretching the duodenal wall and generating a fixed distance between a center of the catheter and the duodenal wall; transmitting a first laser beam in a direction essentially perpendicular to a longitudinal axis of the catheter, towards the duodenal wall, wherein the first laser beam has a first wavelength and a first spot diameter and is configured to cause ablative damage in a region of the duodenal wall as a result of its impingement thereon; transmitting a second laser beam essentially perpendicularly to the longitudinal axis of the catheter, wherein the second laser beam has a second wavelength and a second spot diameter and is configured to detect modifications in the region of the duodenal wall as a result of the impingement of the first laser beam thereon, evaluating the extent of impact on the region of the duodenal wall, based on the detected modifications therein.

According to some embodiments, the first wavelength is in the range of 1450-1600 nm. According to some embodiments, the first wavelength is 1550 nm. According to some embodiments, the second wavelength is 980 nm.

According to some embodiments, the second spot diameter is larger than the first spot diameter, thereby enabling evaluation of ablative damage caused to tissue directly and indirectly affected by the first laser beam.

According to some embodiments, the expandable member may include or be a non-compliant balloon.

According to some embodiments, the second laser beam is transmitted to the region of the duodenal wall at a delay relative to the transmission of the first laser beam to the same region of the duodenal wall.

According to some embodiments, the delay is in the range of 0.1-10 sec.

According to some embodiments, the first and second laser beams are transmitted simultaneously towards different target areas of the duodenal wall.

According to some embodiments, the method may further include rotating a deflective optical element, such that the first and/or second laser beam are deflected toward the duodenal wall in an essentially circumferential pattern.

According to some embodiments, evaluating the extent of impact on the region of the duodenal wall may include determining the depth and/or width of the ablative damage.

According to some embodiments, the method may further include adjusting parameters related to the first laser beam, based on the evaluated extent of impact on the region of the duodenal wall detected by the second laser beam.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions.

BRIEF DESCRIPTION OF THE FIGURES

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION OF THE INVENTION

Figures 1, 2:
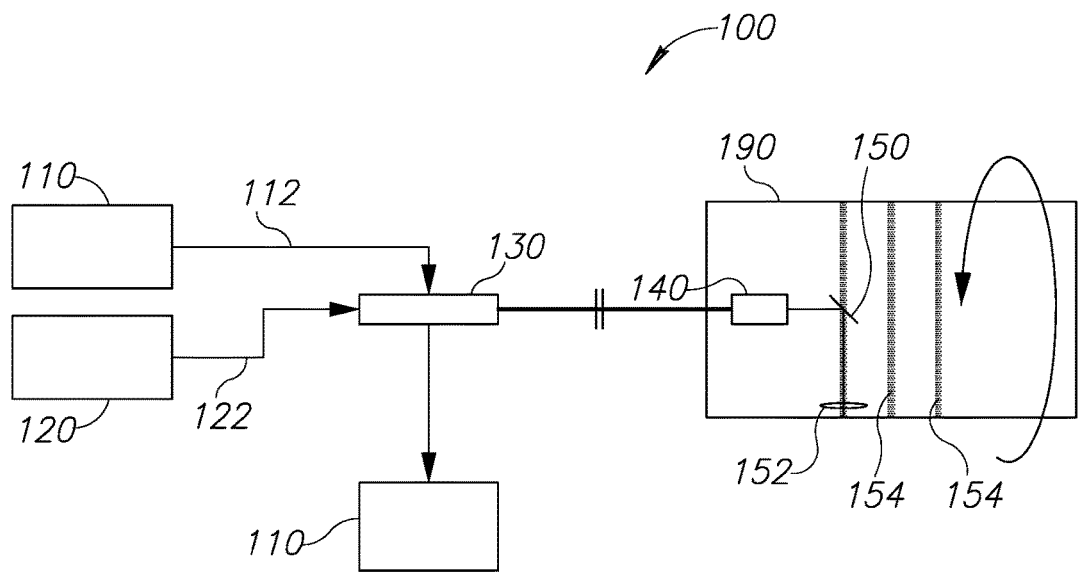
FIG. 1 is an outline of an optical system for ablation of duodenal tissue with real-time ablation feedback, according to some embodiments.
FIG. 2 depicts two optional optical concepts for spatial separation of an ablative beam and a feedback beam configured to evaluate the impact of the ablative beam, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

According to some embodiments, there is provided a device for real-time evaluation of duodenal ablation (or other lumen in the GI tract or pulmonary tract), the device including a catheter comprising an expandable member configured to stretch the duodenal wall and to generate a fixed distance between a center of the catheter and the duodenal wall; and a laser transmitting element coupled with the catheter body and configured to transmit a first laser beam and a second laser beam.

As used herein, the term "duodenum" refers to the part of the small intestine of a vertebrate's gastrointestinal tract which is situated between the stomach and the jejunum. According to some embodiments, the duodenum comprises the pylorus of the stomach. The duodenum includes the lumen and the duodenal wall surrounding the lumen. The duodenal wall includes the following layers from the lumen outwards: the mucosa villi layer, the submucosa layer (which includes the submucosal plexus, the circular muscle layer, the myentric plexus), the longitudinal muscle layer and the peritoneum/mesenteric layer. The combination of the circular muscle layer and longitudinal muscle layer may be referred to herein as the tunica muscularis.

As used herein, the terms "submucosal plexus" and "Meissner's plexus" may be used interchangeably and refer to a neural plexus residing in the submucosa layer of the duodenal wall. Without being bound by any theory, the submucosal plexus transmits neural signals within the duodenum, e.g. to nerves extrinsic to the duodenum, such as, the vagus, duodenal ganglia, sympathetic nerves, and parasympathetic nerves. The submucosal plexus comprises mainly sensory neurons that transmit neural signals obtained from chemical and/or mechanical sensors in the duodenum activated by passage of food through the duodenum.

According to some embodiments, a target region is a region within the duodenal wall that contains sensory neurons. According to some embodiments, the target region includes at least part of the neurons within regions selected from the group consisting of: the myentric plexus, the submucosal plexus, duodenal branches of the vagus nerve, sympathetic nerves innervating the duodenal wall, parasympathetic nerves innervating the duodenal wall, VAN arrays in the duodenal wall and a combination thereof. Each possibility represents a separate embodiment of the present disclosure.

As used herein, the term "catheter" refers to a catheter which is configured to be introduced into the lumen of a duodenum. According to some embodiments, the catheter is configured to be introduced into the lumen of a duodenum through the mouth of a subject. According to some embodiments, the catheter is configured to be introduced through the colon. According to some embodiments, the catheter comprises an endoluminal duodenal catheter. According to some embodiments, the catheter is an endoluminal duodenal catheter. According to some embodiments, the catheter is a laser emitting catheter. According to some embodiments, the laser element is comprised in, and possibly located within, the catheter.

According to some embodiments, the first laser beam may be an ablative laser beam, i.e. a laser beam configured to ablate the tissue upon which it impinges.

According to some embodiments, the second laser beam may be an evaluative and/or feedback laser beam, i.e. a laser beam configured to enable detection of modifications in the tissue caused by the ablative laser beam. According to some embodiments, the second laser beam may scan the ablation lines perpendicularly thereto, optionally at different power densities. According to some embodiments, the second laser beam may scan the ablation lines back and forth, optionally linearly and/or helically. According to some embodiments, the amount of backscattered second laser beam is correlated, optionally linearly, with the degree of ablation and/or modification caused to the tissue. According to some embodiments, the laser transmitting element includes a sensor configured to detect and/or absorb backscattered light of the first and/or second laser beam.

As used herein, the term "ablation" may refer to affecting tissue, by vaporization, chipping, cutting, impacting, denervating, modifying, damaging, severing or other erosive processes or combination of processes, or otherwise impeding at least part of the neurons in the target area. Each possibility is a separate embodiment. According to some embodiments, ablation may refer to a process during which damage is caused to duodenal tissue and/or sensory nerves within the duodenal tissue, by transmitting laser radiation thereon. According to some embodiments, the ablation comprises thermal damage. According to some embodiments, the ablation comprises mechanical damage. According to some embodiments, the ablative laser radiation may be configured to heat the target region to at least 45-75° C. or significantly higher when exposure is very short to induce a more significant injury. According to some embodiments, the ablation may impact neurohormonal and/or other signals triggered by food passing through the gastrointestinal (GI) tract, and thus the subject's sense of satiety and/or hunger and/or hormonal secretion.

According to some embodiments, the first and/or second laser radiation may be pulsed laser radiation. According to some embodiments, the first, ablative laser radiation may be focused on a target area comprising sensory neurons. According to some embodiments, tissue surrounding the target region may remain functional.

According to some embodiments, the first and/or second laser beams may be configured to be transmitted in a direction essentially perpendicularly to the longitudinal axis of the catheter, for example using a prism, a mirror or other suitable deflective element. According to some embodiments, the deflective element, functionally coupled with the laser emitting element, may be configured to direct the laser beam to a region on and/or beneath the duodenal wall. According to some embodiments, the deflective element (e.g. prism or mirror) may be rotatable so as to bring about a circumferential ablation. As used herein, the term "circumferential ablation" or ablation along a circumferential trajectory" may be used interchangeably and may refer to ablation provided around the duodenal wall. According to some embodiments, the circumferential ablation may be circular, i.e. if the laser beam is rotated 360 degrees without movement of the catheter and/or laser emitting element. According to some embodiments, the circumferential ablation may be helical, i.e. if the laser beam is rotated concurrently with forward (or backward) movement of the catheter and/or laser emitting element.

According to some embodiments, the deflective element may deflect the first and/or second laser radiation at an angle of 90 degrees from a longitudinal axis of the catheter. According to some embodiments, the deflective element deflects the first and/or second laser radiation through one or more apertures in the catheter. According to some embodiments, the deflective element may be located within the distal head of the catheter. According to some embodiments, the deflective element may be associated with or be an integral part of the laser transmitting element. According to some embodiments, the deflective element may be rotatable. According to some embodiments, the deflective optical element may direct the laser radiation to a plurality of target areas along a circular trajectory within the duodenal wall or in contact with the duodenal wall. Each possibility represents a separate embodiment of the present disclosure. According to some embodiments, the deflective element may be or include a prism, optionally a rotatable prism. According to some embodiments, the deflective element may be or include a beam-splitter prism. According to some embodiments, the device may further include at least one lens element. According to some embodiments, the lens element is or includes a correction lens configured to correct aberration.

According to some embodiments, the deflective optical/ element may be selected from the group consisting of a wide-angle lens, a dove prism, a reversion or "K" prism, a Delta or Pechan prism, a dispersive prism, a reflective prism, a beam-splitting prism, a deflective prism, a triangular prism, a trapezoidal prism, a Glan-Taylor prism or a Glan-laser prism, a high-powered laser-light right-angle prism, a retroreflector and combinations thereof. Each possibility is a separate embodiment. According to some embodiments, the prism is a low-loss deflective prism. According to some embodiments, the dispersive prism is a triangular, a Pellin-Broca prism, an Abbe Prism or a compound prism. According to some embodiments, the optical element may be a wide-angle lens system capable of correcting f-theta distortion or f-sin(theta) distortion. According to some embodiments, the system further includes a focusing element, optionally positioned before the rotatable optical element, with long enough focal length to enable focusing on a target.

According to some embodiments, the first, ablative laser radiation is a pulsed laser radiation configured to initiate non-linear energy absorption and interaction with the tissue. Without wishing to be bound by any theory or mechanism, short pulsed focused laser radiation directed at a tissue may result in a non-linear interaction with the tissue, such that plasma formation and/or photo-ablation occur only at a site in the tissue in which the energy peak at a given area has an energy flux high enough to cross a pre-determined threshold. According to some embodiments, photo-ablation in the presence of a high enough peak power in the focus area may be accompanied with some level of absorption of the laser beam by adjacent tissue. Non-limiting examples of lasers that may be used to produce such laser radiation include micro Q-Switched Nd:YAG lasers such as, but not limited to, those manufactured by Kigre (MK-367) that are very compact and produce a beam that may cross ablation threshold when sufficiently focused, standard flash pumped Q-Switched lasers (including those that are self Q-Switched), high repetition rate Solid State Diode Pumped Nd:YAG lasers, fiber lasers which use small spots to obtain a high enough peak power to cause damage, or any combination thereof. Each possibility represents a separate embodiment. Other non-limiting examples include CW, quasi CW or Q switched lasers, such as a CW laser in the range of 1550-1570 nm. Appropriate lasers can be, for example, double YAG in 532 nm, or laser diodes of 980 nm or 808 nm, a laser in the 1500 nm range or Holmium/Thuliium lasers at 2 microns.

According to some embodiments, the ablative beam may have a wavelength in the 1300, 1400 nm, 1450-1600 nm, 1530-1590 nm, 1550-1570 nm, 980-1064 nm or 1850-1950 nm range. As a non-limiting example, the ablative beam may have a wavelength of 1550 nm. As another non-limiting example, the ablative beam may have a wavelength of 1064 nm. As another non-limiting example, the ablative beam may have a wavelength of 1067 nm. As another non-limiting example, the ablative beam may have a wavelength of 980 nm.

According to some embodiments, the feedback beam may have a same or a different wavelength than that of the ablative beam. According to some embodiments, the feedback beam may have a wavelength of 532 nm, 780 nm, 808 nm, 980 nm, 1310 nm, 635 nm, 1550-1570 nm, green laser in CW or modulation mode, or blue LED. As a non-limiting example, the feedback beam may have a wavelength of 980 nm with power of less than 1 Watt in CW mode or with modulation of 21-990 Hz. The ablative beam may have a wavelength of 1550-1567 nm with power in the range of 0.1-30 Watts or 3-30 Watts in CW mode or with modulation of 5-100 Hz.

According to some embodiments, the feedback may be based on back reflection and/or scattering of light from the ablated tissue. According to some embodiments, the feedback beam may scan over the ablation lines generated by the rotating ablative laser beam. According to some embodiments, the feedback beam enables evaluating the width of the ablation line, the amplitude of peak of the ablation line, the area of the ablation or any combination thereof. Each possibility is a separate embodiment.

According to some embodiments, a same laser be used for both the ablation and the feedback, for example, the 1550-1567 nm laser listed above. According to some embodiments, a different laser may be used for each of the ablation and the feedback. According to some embodiments, ablation may be performed using a single mode laser (SM) while the feedback may be performed using a multimode laser (MM). According to some embodiments, the ablation fiber is a single mode, while the feedback is based on a multimode fiber configured to provide high depth of focus for the ablation and high collection throughput for the imaging/feedback. According to some embodiments, an SM ablation fiber may be coupled to a core fiber with a controlled/limited increase in beam diameter, i.e., an increase from ~10 micron to 50-200 micron decreasing the beam divergence. According to some embodiments, M-squared increases by no more than times 3-5.

According to some embodiments, the laser emitting element may include two or more optical fibers, namely a first optical fiber configured to transmit the first, ablative laser beam and a second optical fiber configured to transmit the second, evaluative laser beam. According to some embodiments, the pair of fibers may be assembled, for example, in a V-groove, assembled separately or fused to a lens, so as to obtain the targeted displacement, correlating with the required displacement in the image plane, as further described hereinbelow.

According to some embodiments, the fiber configured to transmit the first, ablative radiation may have a smaller core than the fiber used for the feedback radiation, such that the spot diameter of the feedback radiation on the tissue will be larger than the spot diameter of the ablative radiation, as further elaborated herein.

According to some embodiments, the fiber configured to transmit both the first, ablative radiation, and the second, evaluating radiation may have a smaller core than the fiber used for the reading or sensing of the feedback radiation.

According to some embodiments, the laser emitting element may include a double cladded fiber configured to deliver the first, ablative laser beam through the core and the second, evaluative laser beam through the clad.

According to some embodiments, the laser emitting element may include a double cladded fiber configured to deliver the first, ablative laser beam, and the second evaluating beam through the core and sense/read the back reflection of scatter of the evaluative laser beam through the clad.

According to some embodiments, the fiber configured to transmit the ablative radiation may have a smaller core than the fiber used for reading the feedback of the radiation.

As used herein, the term "real-time" refers to an evaluation of the impact caused to tissue, such as duodenal tissue, as a result of transmitting ablative radiation thereon, which is performed during the ablation procedure. According to some embodiments, the real-time evaluation may be performed simultaneously with the ablation, e.g. by co-transmitting ablative radiation and evaluative laser radiation towards a target region. According to some embodiments, the real-time evaluation may be sequential, as further elaborated herein.

According to some embodiments, the real-time evaluation may be performed with sensing the back-scattered light from the ablation process.

According to some embodiments, the feedback beam may enable monitoring and/or identifying at least one parameter related to the ablation of the duodenal tissue. According to some embodiments, the feedback beam may enable monitoring and/or identifying more than one parameter related to the ablation of the duodenal tissue, such as 2, 3, 4, 5, 10 or more parameters. Each possibility is a separate embodiment. Non-limiting examples of suitable parameters which may be evaluated, monitored and/or identified by the feedback beam include: effect of ablation, abnormalities and/or dysfunction in the ablation process (e.g. improper expansion of the expandable member, improper termination of the laser treatment, impaired rotation of the beam, etc.), velocity of beam rotation, diameter of expanded section (e.g. by measuring the diameter of the expandable member once expanded), identification of a previous section that underwent ablation, for example, in order to align repositioning of the expandable member for repetitive interventions, identification of undesired tissue, such as, but not limited to, papilla or any other suitable parameter or combination of parameters. Each possibility is a separate embodiment.

Additionally or alternatively, the evaluation of the ablation may include collection of the back reflected and/or scattered light originating from the ablative laser beam itself, thus obviating the need for an additional laser and/or optical fiber. According to some embodiments, the feedback may include operating the laser transmitting element in a first, ablative mode and then operating the laser transmitting element in a second, evaluating mode, configured to detect and/or collect back reflected and/or scattered radiation. According to some embodiments, the feedback can be based on the amplitude of a reflected beam and/or phase shift and/or noise spectrum and/or noise within a pre-set frequency range, and/or deviation from a pre-set range associated with its reflection/scattering.

According to some embodiments, a laser beam may be used to provide feedback with regards to the impact obtained using other ablative modalities such as, but not limited to, radio frequency (RF) ablation, microwave ablation, ultrasound ablation, thermal ablation, or alike. Each possibility is a separate embodiment.

According to some embodiments, the first, ablative laser beam may have a same or a different spot diameter on the tissue, as compared to the second, evaluative laser beam.

According to some embodiments, the spot diameter of the second, evaluative laser beam may be larger than the spot diameter of the first, ablative laser beam. For example, the first laser beam may have a spot diameter in the range of 10-500 microns, 20-400 microns, 100-400 microns, 100-300 microns, 20-200 microns or any other range of spot diameters in the range of 10-500 microns. Each possibility is a separate embodiment. The second laser beam, on the other hand may, for example, have a spot diameter in the range of 400-1500 microns, 500-1000 microns, 500-750 microns or any other range of spot diameters in the range of 400-1500 microns. Each possibility is a separate embodiment. According to some embodiments, the second, evaluative laser beam may be 1.5-100 times larger, 1.5-50 times larger or 2-25 times larger than the spot diameter of the first, ablative laser beam. Each possibility is a separate embodiment. Such difference in spot size may enable evaluation of tissue adjacent to the tissue directly affected by the ablation, also referred to herein as collaterally affected tissue. As further discussed herein below, having a larger spot diameter may require that the evaluation beam will be delayed relative to the ablation beam.

According to some embodiments, the spot diameter of the second, evaluative laser beam may be smaller than the spot diameter of the first, ablative laser beam. This may serve to ensure that the signal detected by the evaluative laser beam will not be distorted, weakened or otherwise influenced by undamaged tissue or by tissue in which photo thermal and/or photo chemistry processes are yet to occur.

According to some embodiments, the laser emitting element may be configured to transmit the second, evaluative laser beam at a delay. An objective of this embodiment is to enable photo thermal and/or photo chemistry processes to happen prior to the monitoring by the feedback beam, which may be of particular importance if the evaluative laser beam has a larger spot size than the ablative laser beam.

According to some embodiments, the laser emitting element may be configured to transmit the second, evaluative laser beam at a delay of, for example, 0.1-1.0 seconds, 0.1-0.5 seconds, 0.25-0.75 seconds, 0.5-1.0 seconds or any other suitable delay within the range of 0.1-100.0 seconds. Each possibility is a separate embodiment.

According to some embodiments, the delay may be caused by temporarily separating the transmittal of the first and second laser beams, e.g. the transmittal of the second, evaluative laser beam may be delayed by 0.1 seconds with respect to the first, ablative laser beam.

According to some embodiments, the delay may be caused by spatially separating the first (ablative) and second (feedback) laser beams, so that when in motion, the first beam hits the tissue first and the second beam hits it in delay.

According to some embodiments, the optical fibers may be laterally separated by using two optical fibers configured to provide offset laser beams. According to some embodiments, the laser transmitting element may include a separating element, such as, but not limited to, a lens configured to increase the angular spacing e.g. by 500-5000 micron, or 700-3000 micron, when reaching the duodenal wall (approximately 10-25 mm from the center of the catheter). It is understood that the distance between the ablation spot and the feedback spot may be determined by the focal length of the lens and the offset of the fibers, as further described herein. According to some embodiments, the lens may include several lenses, such as, but not limited to, collimation and focusing lenses.

According to some embodiments, the optical fibers may be angularly separated. According to some embodiments, the first (ablative) and second (feedback) laser beams may be overlapping beams angularly separated using a separating element, such as, but not limited to, a dispersive element, a diffractive optical element, a prism or other suitable element configured to selectively separate the first (ablative) and second (feedback) laser beams. According to some embodiments, the distance between the ablation spot and the feedback spot may be determined by the type of separating element used. According to some embodiments, the overlapping beams may be transmitted by two separate optical fibers. According to some embodiments, the overlapping beams may be transmitted by a double cladded fiber.

According to some embodiments, the spot size of the feedback beam may be determined/set by controlling the core diameter of the double cladded fiber and/or by controlling the divergence of the laser light emitted from the fibers.

According to some embodiments, the device may include a lens associated with the feedback beam.

According to some embodiments, the device may further include a rotating shaft configured to rotate the catheter and/or the laser transmitting element or parts thereof (e.g. the deflective element), during the ablation procedure. According to some embodiments, the rotating shaft may be made of at least two sections having a different flexibility. According to some embodiments, the rotating shaft may include a pivoting point. This serves to ensure that if a distal portion of the duodenum is treated before treatment of a more proximal portion, thus requiring backward movement of the catheter, the balloon and/or the laser transmitting element, the part of the shaft that includes the laser transmitting element, is not moved by forces applied to the shaft by proximal segments. That is, the shaft may be configured to withstand and/or remain steady despite forces that are perpendicular to the axis of the lumen/shaft, caused by intestinal movement.

According to some embodiments, the device may include a processing circuitry configured to evaluate the extent of impact on the region of the duodenal wall, based on the detected modifications therein.

According to some embodiments, the processing circuitry may be configured to detect abnormalities and/or dysfunctions in the ablation process, such as, but not limited to, improper expansion of the expandable member, improper termination of the laser treatment, and/or impaired rotation of the beam. Each possibility is a separate embodiment.

Additionally or alternatively, the processing circuitry may be configured to determine and/or monitor the rotational velocity of the ablative beam and/or of the feedback beam on the tissue.

Additionally or alternatively, the processing circuitry may be configured to determine the shape of the size, diameter and/or shape of the expandable member, based on the signals obtained from the feedback beam.

Additionally or alternatively, the processing circuitry may be configured to determine and/or monitor the diameter of the expanded section, for example by measuring the diameter of the expandable member once expanded.

Additionally or alternatively, the processing circuitry may be configured to detect a previously treated section. This may be of uttermost importance when the section of the duodenum requiring treatment extends the length of the expandable member, thus requiring its repositioning.

Additionally or alternatively, the processing circuitry may be configured to enable identification of undesired tissue, such as, but not limited to, the papilla of Vater or any other identifiable anatomy.

According to some embodiments, the processing circuitry may be configured to recommend ablation parameters (e.g. ablation power or pulse frequency), based on the extent of impact on the region of the duodenal wall detected. According to some embodiments, the processing circuitry may be configured to adjust ablation parameters, based on the extent of impact on the region of the duodenal wall detected.

According to some embodiments, the processing circuitry may be configured to correlate the extent of impact detected with histological observations.

According to some embodiments, the processing circuitry may be configured to identify non-target areas (e.g. bile duct or pancreatic duct), ablation of which should be avoided, based on the signal obtained from the feedback beam. According to some embodiments, the processing circuitry may be configured to direct and/or position the catheter, such that ablation of non-target areas is avoided, based on their identification. Additionally or alternatively, the positioning and/or orientation of the catheter and/or of the laser transmitting element may be based on detection of non-target areas by endoscopy or by estimating their location, for example, based on anatomic maps. According to some embodiments, the processing circuitry may be configured to stop and/or halt the beam, when the laser beam reaches non-target areas, and/or an already treated area.

According to some embodiments, the expandable member may be a balloon. According to some embodiments, the balloon may be semi-compliant or non-compliant. According to some embodiments, the balloon may expand the duodenum to a predetermined radius (using a non-complaint balloon) or to a pre-set range of diameters (using semi-complaint balloons), while complying with the shape of the duodenum lumen, along its longitudinal axis. The lack of compliancy of the balloon may be crucial in order to ensure that a pre-determined dose of laser energy be used regardless of angular orientation of the laser beam, such that a uniform ablation across the duodenal surface is obtained. This, since the semi/non-compliant balloon ensures that the rotating beam is derived from the center of the balloon and thus of the duodenum. Ensuring a uniform ablation is complicated by the fact that the inner shaft, used to rotate the beam, is subject to radial forces applied by duodenal sections preceding and following the working area.

According to some embodiments the ablation lines are created when the duodenum is expanded/stretched to a diameter of 25-70 mm. According to some embodiments the diameter is determined by a non-compliant balloon that stretches the duodenum. According to some embodiments, semi or complaint balloons may be used in conjunction with means to determine the diameter so as to ensure that the desired dose may be determined and/or adjusted by modulation of laser power and/or rotational speed.

According to some embodiments, the distance of the laser rotating element to the duodenal wall, the balloon radius, may be 12.5-25 mm, 15-30 mm, 18-25 mm or any other suitable distance within the range of 12.5-35 mm. Each possibility is a separate embodiment. As a non-limiting example, the distance may be 18 mm.

According to some embodiments, the balloon, or other expandable member, may include multiple sections. According to some embodiments, the sections of the balloon may be interconnected by connection points allowing bending (e.g. 120 degrees bending) between sections, so as to enable expansion of the duodenum lumen, while maintaining its 3D shape. According to some embodiments, the segments may be of a same or different lengths and/or diameters to comply with anatomy. According to some embodiments, the angle of balloon wall between segments may be minimized to 15 degrees (+/−5 degrees) to decrease "dead area" between the segments, as illustrated hereinbelow. According to some embodiments, the connection points (also referred to as bending sites) may serve as landing/support zones or axial sites for the rotating shaft.

According to some embodiments, the segments of the balloon may be inflated simultaneously or sequentially. According to some embodiments, the distal segment may be configured to be first inflated so as to enable the application of push forces and extension of the catheter at the end of the catheter closest to the ablation target (e.g. the beginning of the duodenum after the pylorus junction). According to some embodiments, the forces applied to stretch/extend the catheter and duodenum may be by air pressure applied by an endoscope. According to some embodiments, the inner shaft may be used to stretch the catheter by applying a pushing force on or towards the distal part of the catheter.

According to some embodiments, the balloon distal facet is used as an anchor to stabilize the axis of the central shaft and is kept in place using the pressure of the balloon.

According to some embodiments, the balloon (or optionally sections thereof) may be coated with parylene to increase thermal resistance, to deal with heating effects on the tissue exposed to the ablating laser beam, thus protecting the balloon from being damaged.

According to some embodiments, the balloon may include longitudinal lines configured to enable determining the rotational speed of the first and/or second laser beam and/or the diameter of the balloon. According to some embodiments, the angular velocity of the ablative beam may be determined by measuring the modulation frequency of the feedback obtained from those lines upon rotation. According to some embodiments, the longitudinal lines may be positioned at an external or internal surface of the balloon. According to some embodiments, the longitudinal lines may be made of metal, dyes, thermal based marks or other material that does not expand, in order to ensure that the longitudinal lines maintain a constant width required to enable determination of balloon diameter. This, by measuring the time it takes to cross the ablation line, when the angular velocity is known, as linear velocity increases with diameter increase and thus decreases the time required to scan the line.

According to some embodiments, a semi-complaint or a complaint balloon maybe used instead of a non-complaint or a semi-compliant balloon to enable larger flexibility regarding the balloon diameter. This may enable using lower profile catheters, as a less stretched balloon, when compressed, can be accommodated in a smaller profile catheter than a large PET balloon that can expand to 30-50 mm in diameter. Accordingly, means are required to determine the diameter of the extended balloon at the target to make sure the desired dose of ablation is applied.

According to some embodiments, the balloon may include circumferential lines (width bands) configured to determine the linear velocity of the catheter and/or of the laser transmitting element.

According to some embodiments, interruption and/or divergences in the signal obtained from back reflection of radiation from the longitudinal and/or circumferential lines may be used to detect rotational impairment, balloon malfunction, malfunctioning optics, or any other suitable parameter or combination of parameters.

According to some embodiments, radiation, back-reflected from longitudinal and/or circumferential lines, may be used to calibrate the intensity of a laser beam used for ablation and/or feedback. According to some embodiments, free-space or fiber beam splitters may be used. In such case, one of the channels that does not get to the sample can be used for calibration. According to some embodiments, the arm of the fiber splitter that projects the beam that is not directed to the tissue may be used to monitor the intensity of the laser beam that is directed to the tissue and to normalize for fluctuations/changes in the laser intensity and/or control laser power.

Additionally or alternatively, imaging elements such as CMOS or CCD cameras may be used to detect impeded and/or halted rotation of the beam, by detecting a frozen video signal.

According to some embodiments, the device may include a support member configured to stabilize the laser transmitting element within the expandable member (e.g. within the balloon). According to some embodiments, the support member may be made from a shape memory material, such as, but not limited to, nitinol.

In some embodiments, the inner wire is introduced into the balloon/s to either: (i) pull the catheter to the distal end and to apply tension when pulled back by the motor that pulls the shaft and maintains tension on the wire connected to the tip of the shaft to keep it centralized or, (ii) have at least one but preferably 2 or 3 wires maintained at a minimal tension, the wire(s) acting as a rail(s) for the tip of the catheter that slides over it/them or, (iii) a string that applies pulling forces to the distal rotating tip to assure it is in the center of the balloon and in an orientation which is parallel to the lumen axis. The pulling forces can be obtained, for example, from a rubber or an appropriate metal coil.

In some embodiments, means to detect the macro 3D shape of the multi-balloon structure in the duodenum are included to enable detecting position and orientation vs other geometrical structures, such as to detect the angle/direction of the major duodenal papilla (an opening of the pancreatic duct into the duodenum) to disable laser firing in this area. This may advantageously enable detecting the position of the papilla and avoiding ablation in this area, thus mitigating the risk of blocking passage of bile and pancreas secretions into the duodenum. This can be based on one or more means such as: (i) use of optical means, such as the feedback signal, to detect its position; (ii) detecting the position of the pulling wire that obtains its position according the lesser curvature (and thereby the associated macroscopic orientation). Detecting the position of the papilla can be achieved by determining the inner curvature of the duodenum—because of the anatomy structure of the bile duct. Determining the inner curvature of the duodenum can be achieved by stretching a wire inside the balloon; this wire would naturally take the inner curvature side between two bending points; identifying this wire can be achieved by using the endoscope or any other image of the positioning of the balloon, or by the feedback mechanism enclosed, which can identify the wire angle, as described below.

Reference is now made to FIG. 1, which is an outline of an optical system 100 for ablating duodenal tissue (or other lumen in the GI or pulmonary tract), with real-time ablation feedback, according to some embodiments. System 100 includes a first laser 110 configured to emit a first laser beam 112 configured to cause ablation of tissue upon which it impinges. First laser beam 112 may, for example, have a wavelength of about 1550 nm and a power of 10 W. System 100 also includes a second laser 120 configured to emit a second laser beam 122 the backscattered light of which enables evaluation of tissue modifications caused due to the ablation. Second laser beam 122 may, for example, have a wavelength of about 980 nm and a fixed power density on the target. First laser beam 112 and second laser beam 122 are directed to a first optical element, here wavelength-division multiplexing (WDM) system 130, which multiplexes a number of optical carrier signals onto a single optical fiber and demultiplexes (splits them apart) at exit. WDM 130 enables bidirectional communications and thus enables receiving part of second laser beam 122 back reflected from the tissue, and to send, as illustrated by arrow 124, the reflected beam to a sensor 126 configured to detect the intensity thereof. When exiting WDM system 130, first laser beam 112 and second laser beam 122 reach a second optical element, also referred to herein as a laser transmitting element 140. Laser transmitting element 140 is configured to generate a spatial separation between first laser beam 112 and second laser beam 122, as further described in FIG. 2 hereinbelow, thus enabling a delay between the ablative first laser beam 112 and the feedback beam 122. The beams are subsequently deflected using a third, deflective optical element 150 (such as, but not limited to, a mirror or a prism), configured to deflect first laser beam 112 and second laser beam 122 at an angle of essentially 90 degrees, whereafter they are focused on a target area in the duodenal wall (illustrated by box 190), by lens 152. Importantly, in order to satisfy a 1.8 mm maximal diameter of the optical fiber, and in order to maximize the spatial separation between the beams, laser transmitting element 140 should preferably be positioned before deflective element 150. Deflective element 150 may be rotatable, such that first laser beam 112 and second laser beam 122 are deflected circumferentially around the duodenal wall, such that first laser beam 112 generates ablative lines 154. Ablative lines 154 cause a different backscattering of second laser beam 122 than untreated tissue. The power intensity of the back reflected part of laser beam 122, detected by sensor 126, may thus be used to evaluate the extent of ablative damage/modification caused.

Reference is now made to FIG. 2 which depicts two optional optical concepts (suitable for use as laser transmitting element 140) for spatial separation of an ablative laser beam, such as first laser beam 112, and a feedback beam, such as second laser beam 122.

According to the first concept, the spatial separation of the beams may be achieved through lateral separation of the laser beams. That is, at initiation the laser beams may be off-set, e.g. by using two separate optical fibers. Due to their initial off-set, the beams impinge upon a separating element, such as, but not limited to, a collimating lens, at a different position, thereby causing, for example, the ablative beam to be displaced and/or diverged relative to the feedback beam. It is understood that according to this embodiment, the degree of separation may be determined by the initial off-set of the laser beams and/or the focal length (degree of divergence) of the beams. It is further understood that, in order to maximize the return acceptance angle, the feedback beam should preferably be centered on the beam.

According to the second concept, the spatial separation of the beams may be achieved through angular separation of the laser beams. That is, at initiation, the laser beams may be overlapping, for example by using a double-cladded optical fiber and pass through a lens together. In this case, a separating element in the form of a dispersive element, a DOE, a prism or other optical element allowing wavelength discriminative refraction of the beams, may be included. The element may specifically refract and/or displace e.g. the ablative beam, while allowing the feedback beam to pass non-diverged. It is understood that according to this embodiment, the degree of separation may be determined by the type dispersive element utilized.

Figure 3:
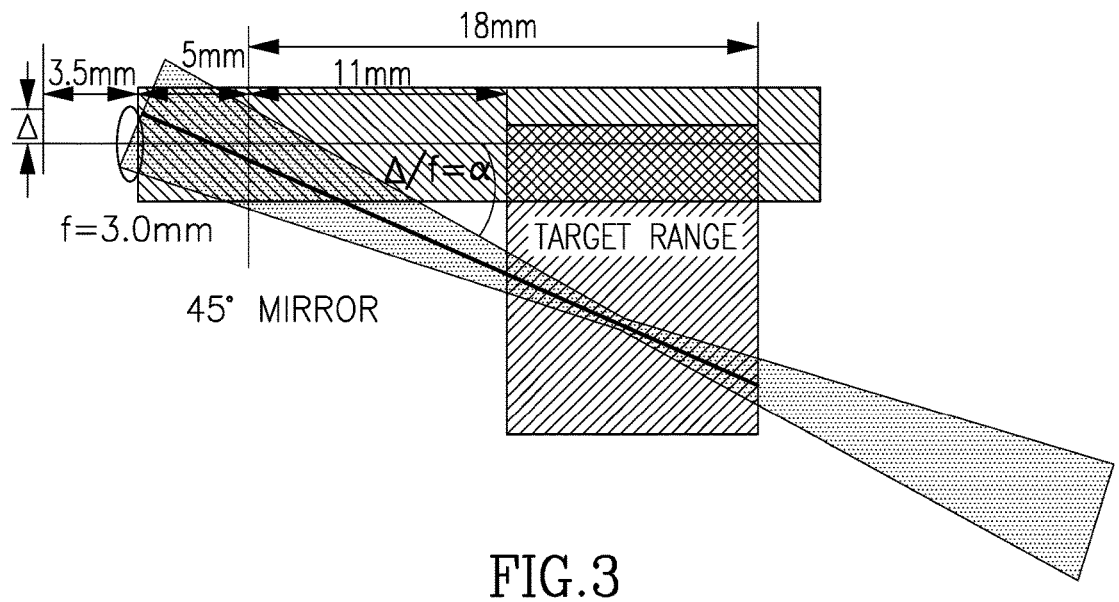
FIG. 3 depicts an example of lateral beam separation with respect to a target area in the duodenal wall, according to some embodiments.

According to some embodiments, the separation between the points of impact of the ablative and the feedback beams is further determined by the distance between the center of the catheter, from which the laser radiation is transmitted, and the target area in the duodenal wall, which again is dependent on the diameter/radius of the expandable member (e.g. 16-23 mm), as illustratively depicted in FIG. 3. In addition, it is understood that the magnitude of the delay between the ablative beam and the feedback beam, at a specific point on the duodenal wall, may be determined by the degree of beam separation as well as the rotational speed.

Figure 4:
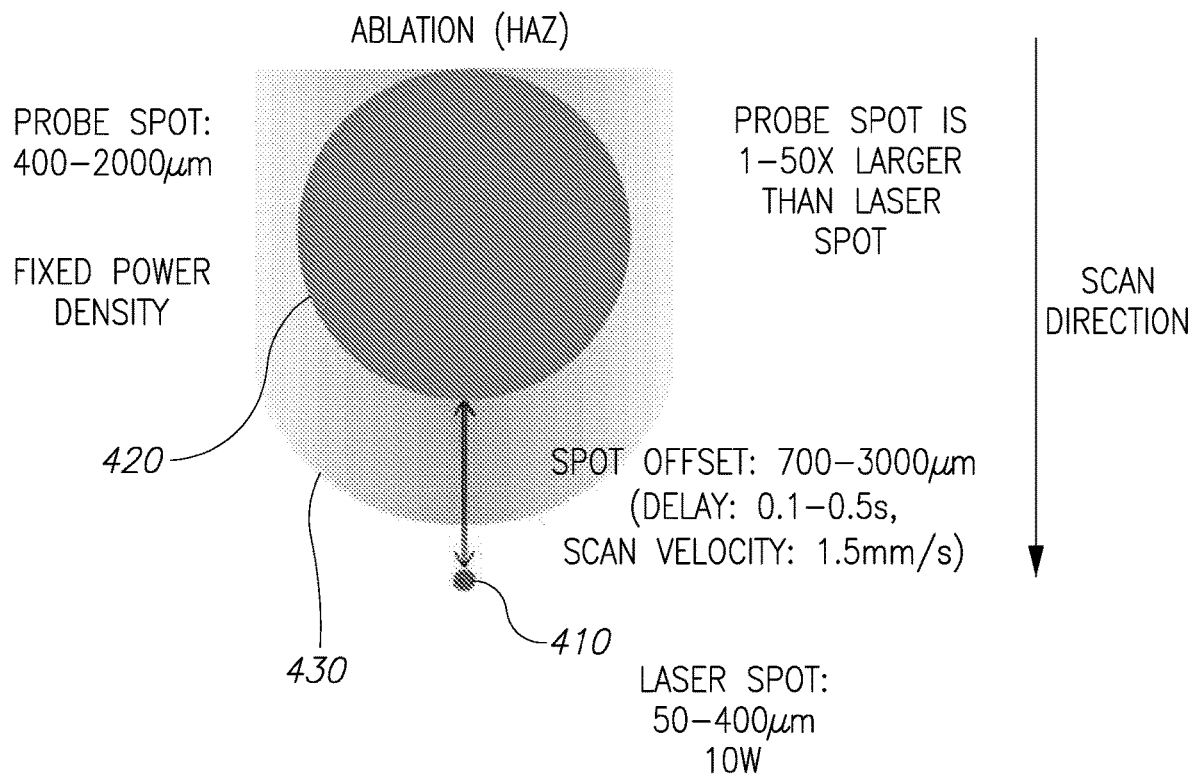
FIG. 4, schematically illustrates a difference in spot diameter of the ablative and evaluative laser beams, according to some embodiments.

According to some embodiments, in order to evaluate photo thermal and/or photo chemistry processes occurring in tissue adjacent to the point of impact of the ablative beam, the feedback beam may have a larger spot diameter than that of the ablative beam, as illustrated in FIG. 4, which schematically illustrates a difference in spot diameter, here a feedback (probe) spot diameter 420 of 400-2000 microns and an ablation spot diameter 410 of 50-200 microns. The difference in spot diameter may be achieved, for example, by using an optical fiber having a larger core diameter for the feedback beam, as compared to the ablative beam. Alternatively, in the case of using a double cladded fiber, the ablative beam may be transmitted through the core of the double cladded fiber, whereas the feedback beam may be transmitted (and collected) through the clad. Yet, in another alternative, both laser beams are transmitted through the core fiber, and clad is used to collect scattering light from the ablation spot. According to some embodiments, due to a delay of x0.1-0.5 s, obtained for example by a spot separation of 700-3000 microns and a scan velocity of 1.5 mm/s, sufficient time passes for photo thermal and/or photo chemistry processes to take place, prior to the feedback beam reaching the region of impact. In addition, due to larger spot diameter of the feedback beam, almost an entire region of impact may be evaluated, such as region of impact 430 caused by a previous impingement of the laser beam.

Figure 5A:
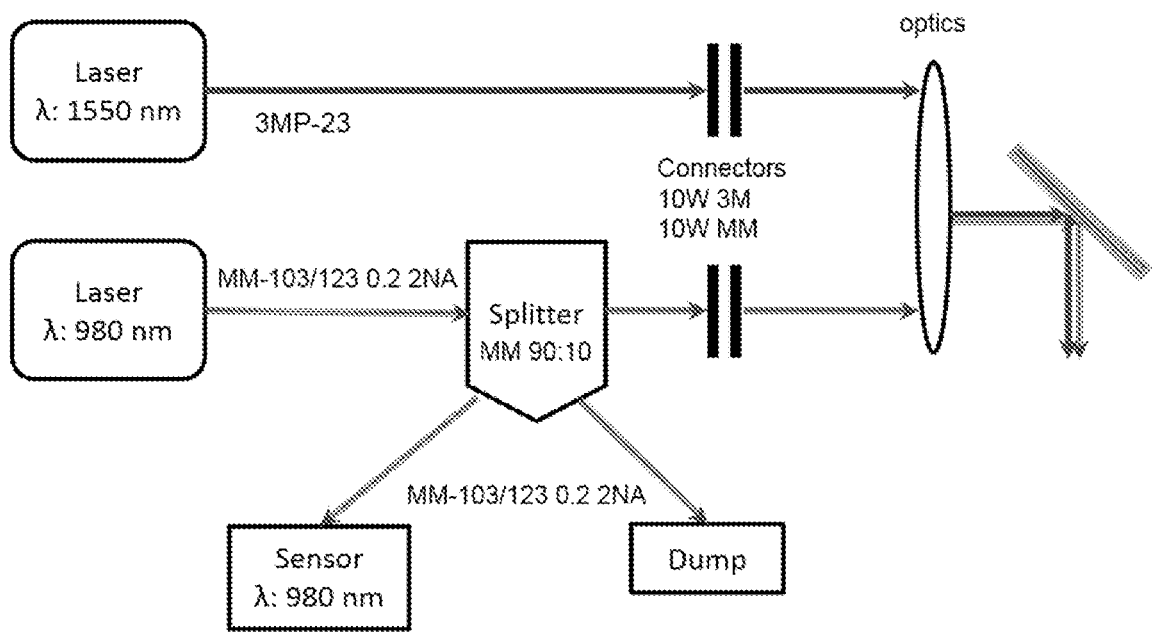
FIG. 5A schematically depicts a setup utilizing two separate optical fibers for delivering the ablative and the feedback beams; according to some embodiments.
Figure 5B:
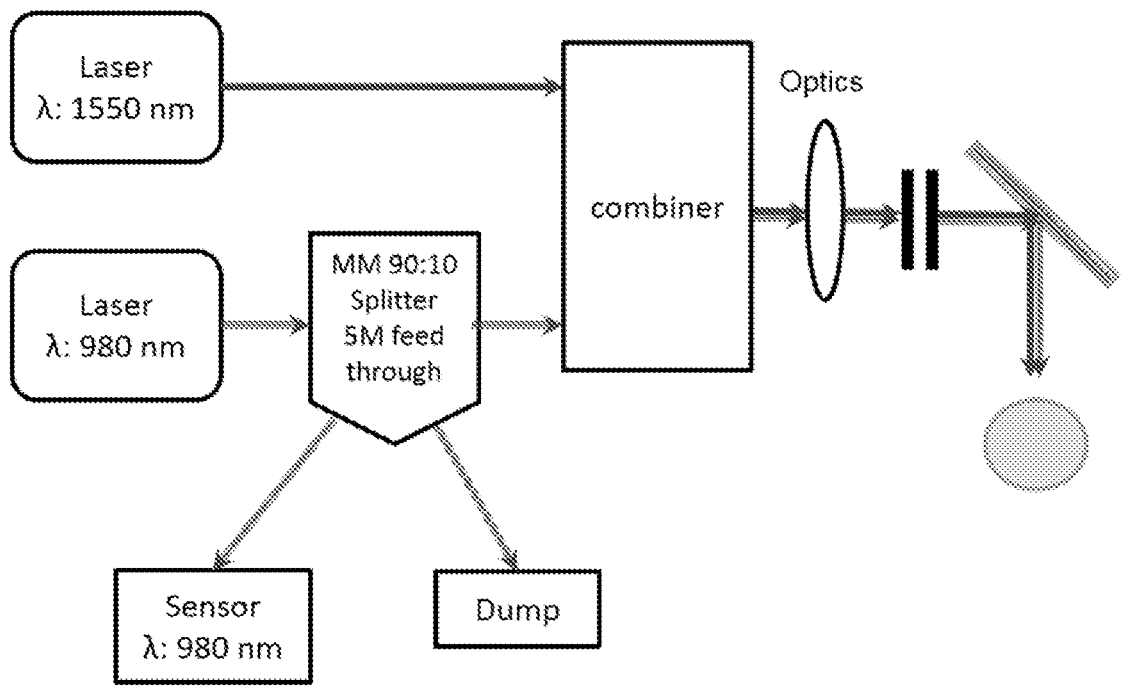
FIG. 5B schematically depicts a setup utilizing a combiner (e.g. a double cladded optical fiber; according to some embodiments.

Reference is now made to FIG. 5A and FIG. 5B, which illustratively depicts a setup 500a suitable when using two separate optical fibers for delivering the ablative and the feedback beams and a setup 500b suitable when using a combiner (e.g. a double cladded optical fiber), respectively. According to some embodiments, a significant difference in spot diameter between the ablative beam and the feed beam is more easily achieved using separate optical fibers, as depicted in setup 500a as compared to setup 500b.

Figure 6:
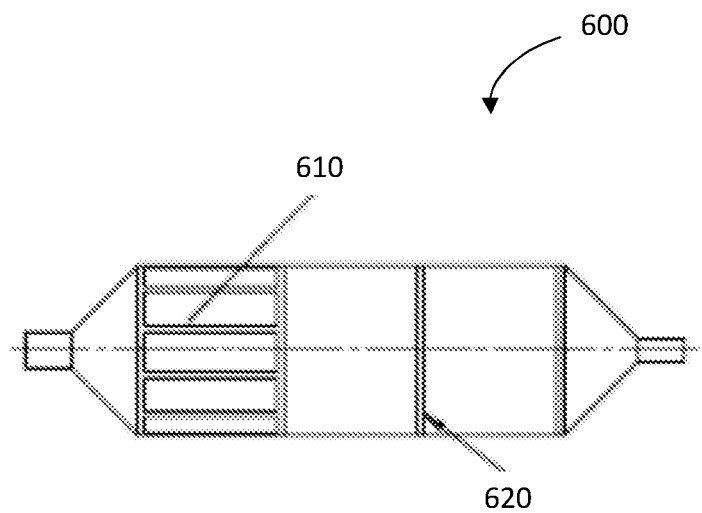
FIG. 6, schematically illustrates a balloon configured to stretch and/or widen the duodenum to a predetermined diameter or range of diameters, according to some embodiments.

Reference is now made to FIG. 6, which schematically illustrates an expandable member, here a balloon 600, configured to stretch and/or widen the duodenum to a predetermined diameter or range of diameters, according to some embodiments. According to some embodiments, balloon 600 may include longitudinal marks 610. Longitudinal marks 610 may be configured to enable determining the rotational speed of the first and/or second laser beam and/or the diameter of the balloon. According to some embodiments, the angular velocity of the ablative beam may be determined by measuring the modulation frequency of the feedback obtained from lines 610 upon rotation. According to some embodiments, longitudinal lines 610 may be positioned at an external or internal surface of the balloon. According to some embodiments, the longitudinal lines may be made of metal, dyes, thermal based marks or other material that does not expand, in order to ensure that the longitudinal lines maintain a constant width required to enable determination of balloon diameter. According to some embodiments, balloon 600 may further include circumferential lines (width bands) 620 configured to determine that linear velocity of the catheter and/or of the laser transmitting element. According to some embodiments, balloon 610 may be coated with parylene to increase thermal resistance, to deal with heating effects on the tissue exposed to the ablating laser beam and/or to direct the laser beam.

Figure 7:
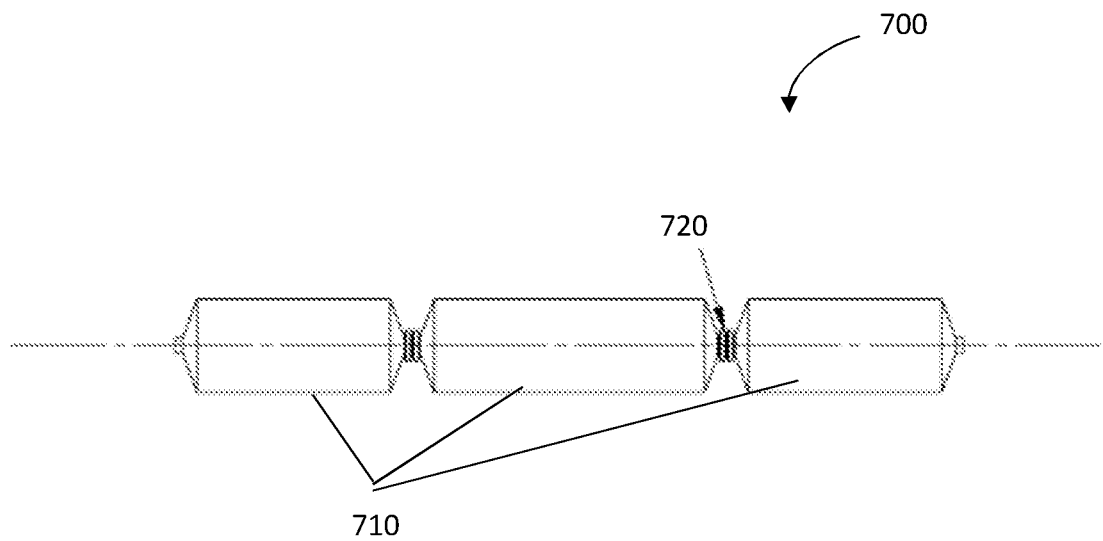
FIG. 7 schematically illustrates a balloon configured to stretch and/or widen the duodenum to a predetermined diameter or range of diameters, having multiple balloon segments, according to some embodiments.
Figure 8A:
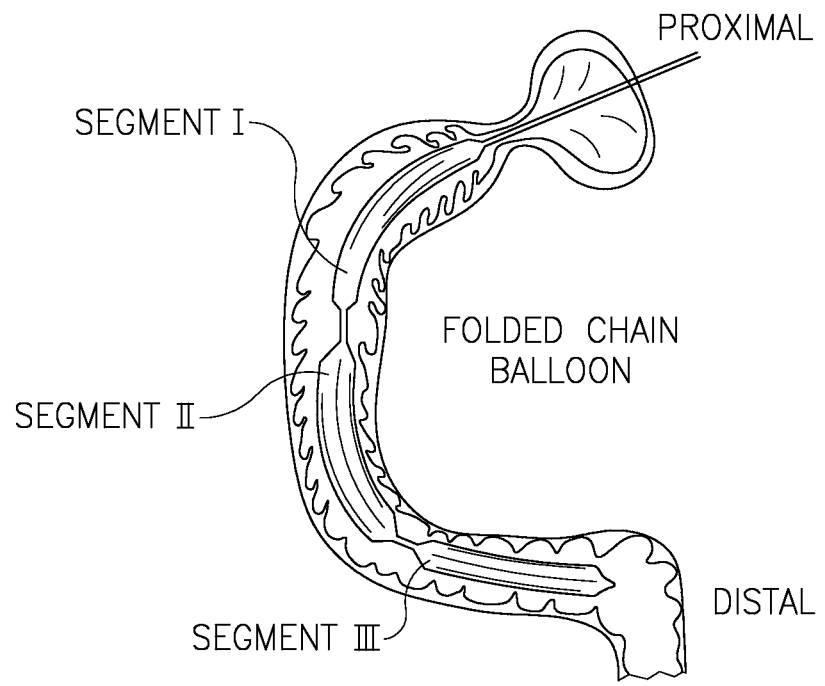
FIG. 8A schematically illustrates a balloon with multiple balloon sections within a duodenum lumen, on its folded configuration, according to some embodiments.
Figure 8B:
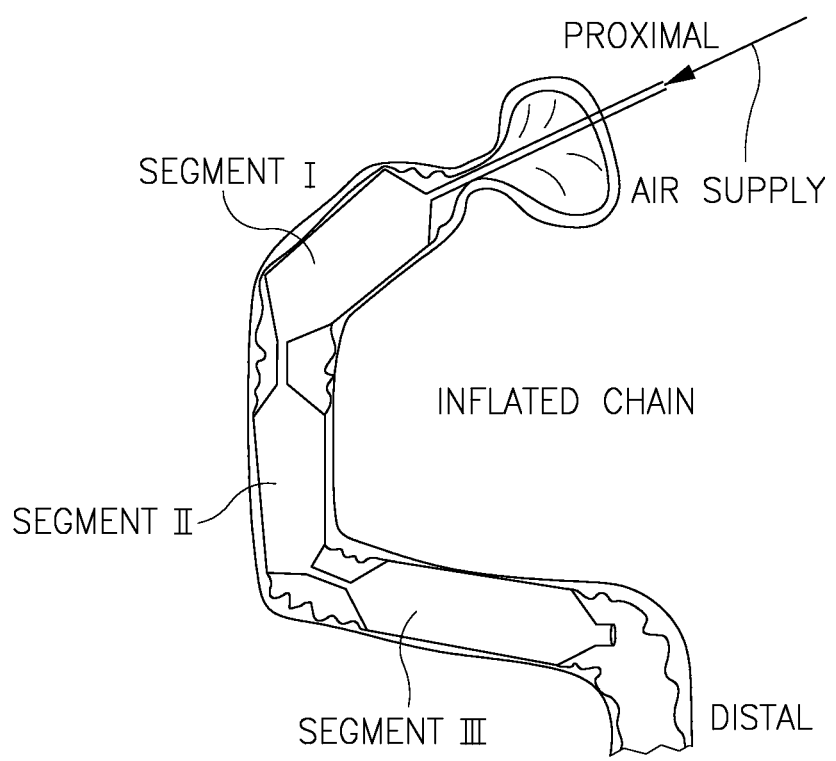
FIG. 8B schematically illustrates a balloon with multiple balloon sections within a duodenum lumen, on its expanded/inflated configuration, according to some embodiments.

Reference is now made to FIG. 7, which schematically illustrates a balloon 700 having multiple balloon segments 710, here illustrated as three balloon segments. According to some embodiments, balloon segments 710 may be interconnected by connection points 720 allowing bending (e.g. 120 degrees bending) there between, so as to enable expansion of the duodenum lumen, while maintaining its 3D shape in both its folded and its inflated configuration, as shown in FIG. 8A and FIG. 8B, respectively. According to some embodiments, balloon segments 710 may have an essentially same length and/or diameter, as here illustrated, and/or be of different length and/or diameters to comply with anatomy, option not shown. According to some embodiments, balloon segments 710 may be inflated simultaneously or sequentially. According to some embodiments, a distal of balloon segments 710 may be configured to be first inflated so as to enable the application of push forces and extension of the catheter at the end of the catheter closest to the ablation target (e.g. the beginning of the duodenum after the pylorus junction). According to some embodiments, each balloon segment, or some balloon segments (e.g. the distal most balloon segment) may include longitudinal and/or circumferential marks, as described in FIG. 6. According to some embodiments, balloon segments 710 may be coated with parylene to increase thermal resistance, to deal with eating effects on the tissue exposed to the ablating laser beam and/or to direct the laser beam.

Figure 9:
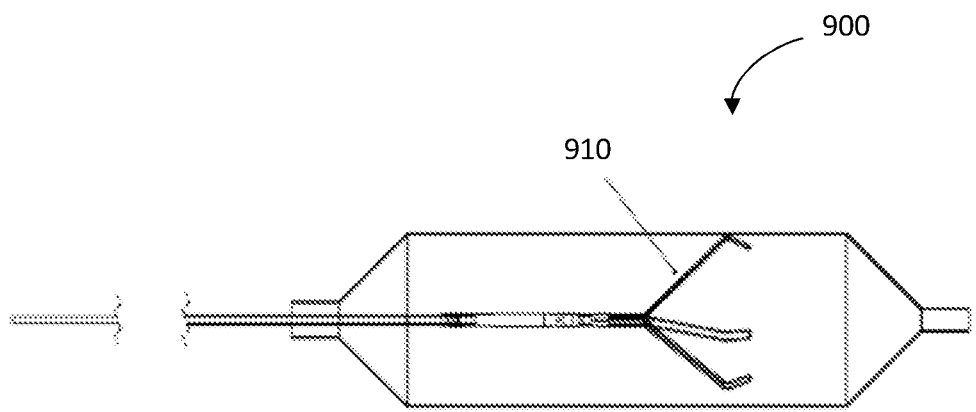
FIG. 9, schematically illustrates a balloon configured to stretch and/or widen the duodenum to a predetermined diameter or range of diameters, the balloon including a support member configured to stabilize the laser transmitting element within the center of the balloon, according to some embodiments.

Reference is now made to FIG. 9, which schematically illustrates an expandable member, here a balloon 900, configured to stretch and/or widen the duodenum to a predetermined diameter or range of diameters, according to some embodiments. Balloon 900 includes a support member 910 configured to stabilize the laser transmitting element within balloon 900. According to some embodiments, the support member may be made from a shape memory material, such as, but not limited to, nitinol.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising", when used in this specification, specify the presence of stated features, integers, steps, operations, elements, or components, but do not preclude or rule out the presence or addition of one or more other features, integers, steps, operations, elements, components, or groups thereof. According to some embodiments, the term "comprising" may be replaced by the term "consisting essentially of" or "consisting of".

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

EXAMPLES

Example 1

Correlation Between Ablation Power and Detected Feedback Signal Power

Figure 10:
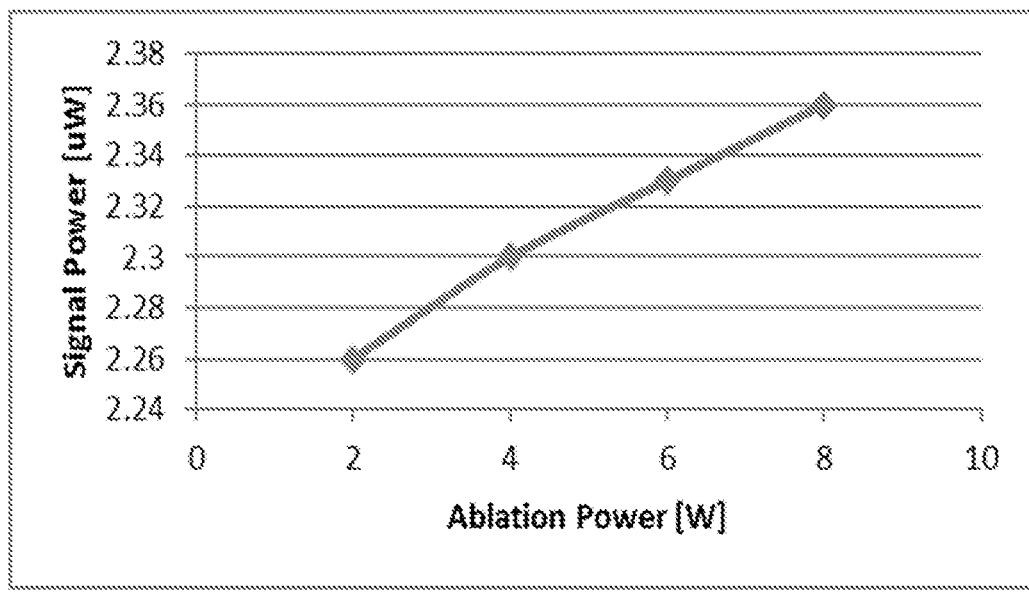
FIG. 10 depicts the correlation obtained between ablation power and detected feedback signal power, using the optical setup depicted in FIG. 5A.

The ability of the herein disclosed system to evaluate ablative impact is demonstrated in FIG. 10, which shows an essentially linear correlation between ablation power and the intensity of the signal detected by the feedback sensor, using the setup depicted in FIG. 5A. This clearly indicates that the ablation/feedback system disclosed herein can be utilized to evaluate the extent of impact of an ablative beam on duodenal tissue.

Example 2

Ex-Vivo Off-Line Analyses of Duodenal Ablation

Figure 11A:
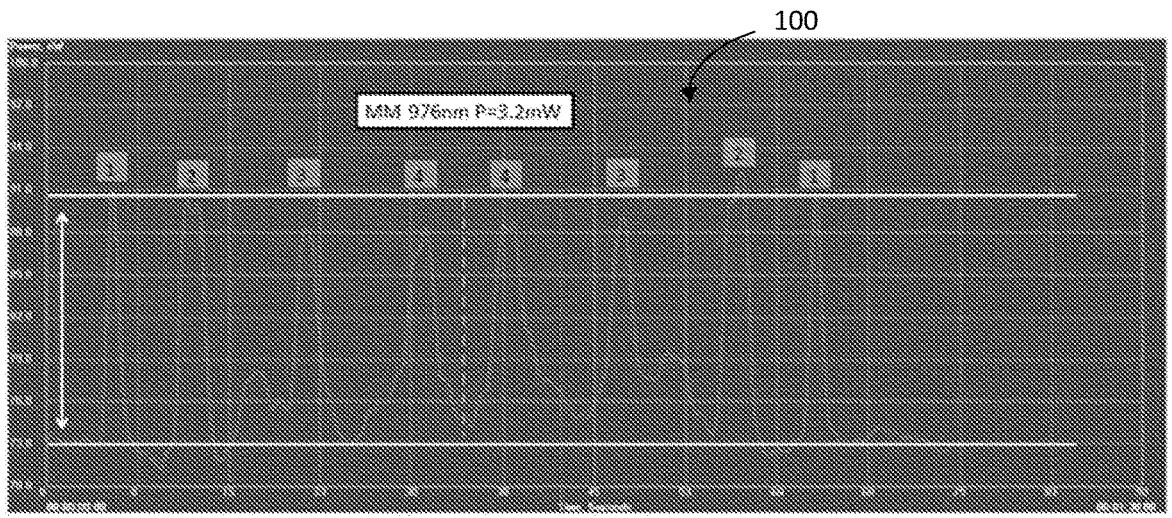
FIG. 11A shows the results obtained from off-line evaluation of duodenum ablation using a laser emitting a feedback beam.
Figure 11B:
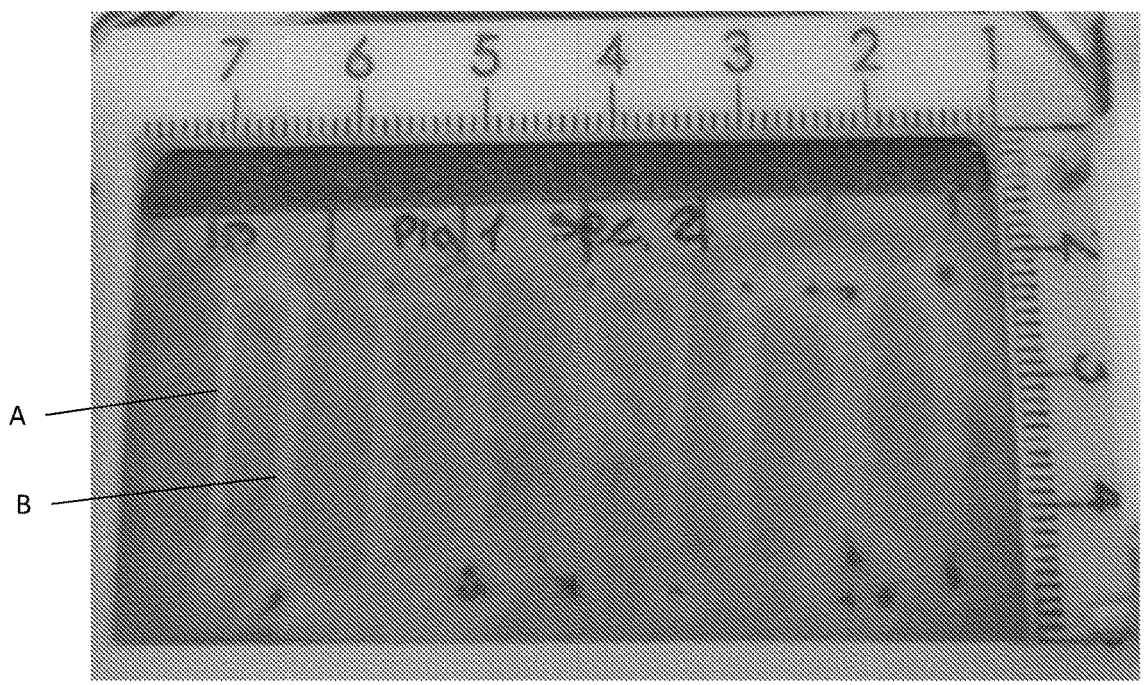
FIG. 11B shows the results obtained from off-line evaluation of the duodenum ablation using visual observation.

An ex-vivo analysis was conducted on a duodenum tissue segment which was ablated using a single mode laser beam as essentially described herein. Following the ablation, a second feedback beam was used to scan the ablation lines perpendicularly at constant speed, as essentially described herein. As seen in FIG. 11A and FIG. 11B, different feedback intensities were readily detectable, for non-ablated vs. ablated tissue. Furthermore, a comparison of the figures demonstrated that ablation lines which are visually observed as thin ablation lines, such as ablation line A, provided a narrow feedback curve, such feedback curve 1. Similarly, ablation lines observed as wider ablation lines, such as ablation line B, appeared as a wider ablation curve 2, when scanned by laser. This clearly shows, that the ablative/feedback system disclosed herein provides a reliable and quantitative evaluation of the ablative impact on the tissue.

Example 3

In-Vivo Real-Time Analyses of Duodenal Ablation

In this example, a standard catheter was used to collect the back scattered/back reflected beam during in-vivo tissue ablation of a pig duodenum using a 1550 nm, 10 W laser. Concurrently with ablation (at a predetermined delay), the ablative impact on the duodenal tissue was evaluated using a second laser, having a wavelength of 980 nm, as essentially described in in FIG. 5A, with lateral separation of the beams.

Figure 12:
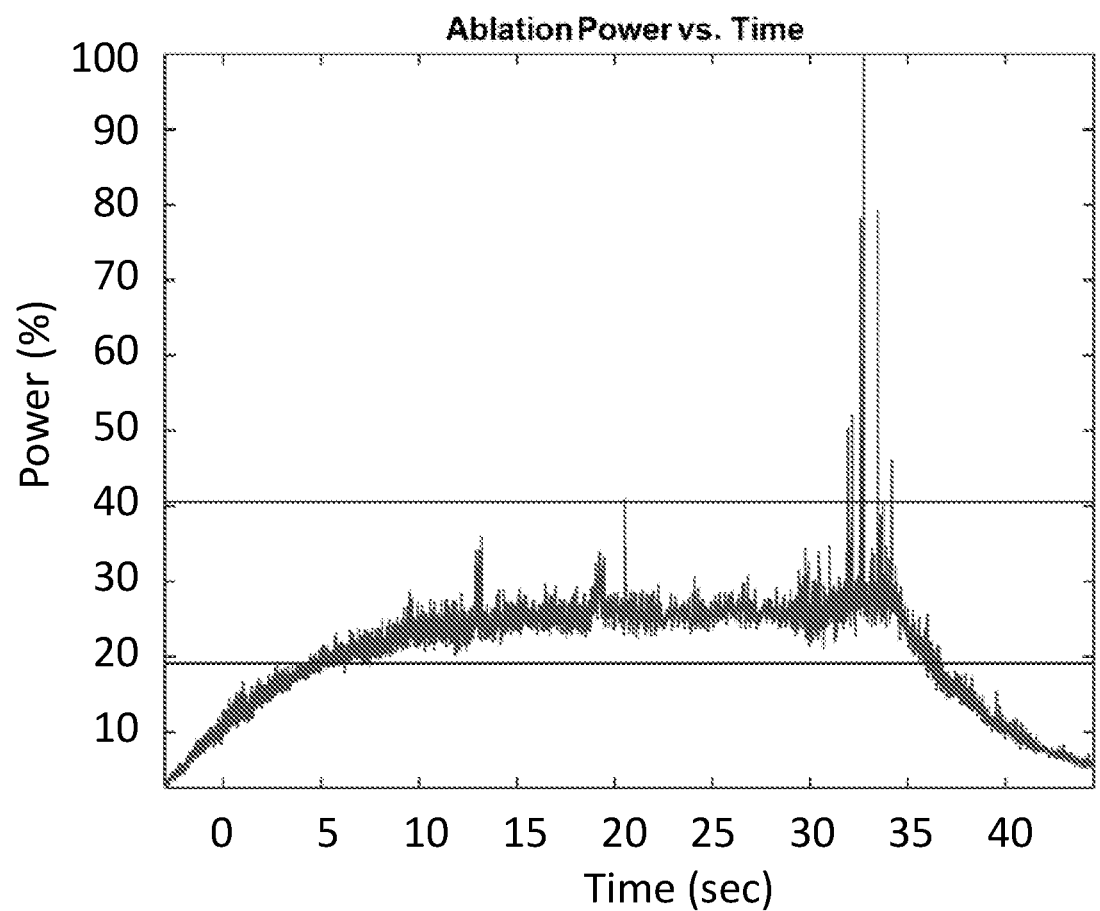
FIG. 12 shows a chart of the evaluation of the power intensity of the feeback beam.

As seen from FIG. 12, evaluation of the power intensity of the feedback beam clearly showed an overall homogenous ablation of the duodenal tissue. Furthermore, at one point, during which the ablative laser beam was directed to a same target area for a prolonged period of time, an ablation crossing an upper ablation threshold level (indicated by horizontal line T2), was readily identified. This result clearly demonstrates that the system and method for ablative feedback evaluation, disclosed herein, enables immediate identification of excessive ablation events, thus enabling halting and/or terminating the ablation procedure prior to damage (such as, but not limited to, perforation) being caused to the tissue.

The examples described above are non-limiting examples and are not intended to limit the scope of the disclosure. The described examples may comprise different features, not all of which are required in all embodiments of the disclosure.

The invention claimed is:

1. A device for real-time evaluation of duodenal ablation, the device comprising: a catheter comprising an expandable member configured to stretch a duodenal wall and to generate a fixed distance between a center of the catheter and the duodenal wall; a laser transmitting element configured to couple to the catheter and to transmit a first laser beam and a second laser beam; wherein the first laser beam has a first wavelength and a first spot diameter and is configured to cause ablative damage in a region of the duodenal wall as a result of its impingement thereon, and wherein the second laser beam has a second wavelength and a second spot diameter and is configured to detect modifications in the region of the duodenal wall resulting from the impingement of the first laser beam thereon; and a rotatable deflective optical element functionally coupled with a laser emitting element and configured to direct the first and/or second laser beam to a region on and/or beneath the duodenal wall; wherein the first and second laser beams are transmitted towards different target areas of the duodenal wall such that during rotation of the deflective optical element, the second laser beam impinges on a given target area at a delay relative to the impingement of the first laser beam at a same given area; wherein the second spot diameter is larger than the first spot diameter, thereby enabling evaluation of ablative damage caused to tissue directly and indirectly affected by the first laser beam.

2. The device of claim 1, wherein said laser emitting element comprises a first optical fiber configured to transmit the first laser beam and a second optical fiber configured to transmit the second laser beam, wherein said first and second fibers are spatially off-set.

3. The device of claim 2, wherein the laser transmitting element further comprises a lens configured to deflect the first laser beam, such that the first and second laser beams are transmitted towards different target areas of the duodenal wall and/or such that said second laser beam impinges on a given target area at a delay relative to the impingement of the first laser beam, when said deflective optical elements are rotated.

4. The device of claim 1, wherein said laser emitting element comprises a double cladded fiber, wherein the first laser beam is delivered through a core of said double cladded fiber and wherein said second beam is delivered through the clad of said double cladded fiber.

5. The device of claim 4, wherein the laser transmitting element further comprises a dispersive element configured to selectively refract said first and/or second laser beam, such that the first and second laser beams are transmitted towards different target areas of the duodenal wall and/or such that said second laser beam impinges on a given target area at a delay relative to the impingement of the first laser beam, when said deflective optical elements are rotated.

6. The device of claim 1, wherein the first wavelength is 1550 nm or 1567 nm.

7. The device of claim 1, wherein the second wavelength is 980 nm.

8. The device of claim 1, further comprising a processing circuitry configured to evaluate an extent of impact on the region of the duodenal wall, based on the detected modifications therein.

9. A method for real-time evaluation of duodenal ablation, the method comprising: inserting a catheter into a duodenum of a subject; deploying an expandable member delivered by the catheter, thereby stretching a duodenal wall and generating a fixed distance between a center of the catheter and the duodenal wall; transmitting a first laser beam in a direction essentially perpendicular to a longitudinal axis of the catheter, towards the duodenal wall, wherein the first laser beam has a first wavelength and a first spot diameter and is configured to cause ablative damage in a region of the duodenal wall as a result of its impingement thereon; transmitting a second laser beam essentially perpendicularly to the longitudinal axis of the catheter, wherein the second laser beam has a second wavelength and a second spot diameter and is configured to detect modifications in the region of the duodenal wall as a result of the impingement of the first laser beam thereon, wherein the first and second laser beams are transmitted towards different target areas of the duodenal wall such that during rotation of a deflective optical element, the second laser beam impinges on a given target area at a delay relative to the impingement of the first laser beam at a same given area; and evaluating an extent of impact on the region of the duodenal wall, based on the detected modifications therein, wherein the first and/or second laser beam are directed using the deflective optical element; wherein the second spot diameter is larger than the first spot diameter, thereby enabling evaluation of ablative damage caused to tissue directly and indirectly affected by the first laser beam.

10. The method of claim 9, wherein the first wavelength is in the range of 1450-1600 nm.

11. The method of claim 10, wherein the first wavelength is 1550 nm and wherein the second wavelength is 980 nm.

12. The method of claim 9, wherein the second spot diameter is larger than the first spot diameter, thereby enabling evaluation of ablative damage caused to tissue directly and indirectly affected by the first laser beam.

13. The method of claim 9, wherein the expandable member comprises a non-compliant balloon.

14. The method of claim 9, wherein the second laser beam is transmitted to said region of the duodenal wall at a delay relative to the transmission of the first laser beam to said region of the duodenal wall.

15. The method of claim 14, wherein the delay is in the range of 0.1-10 sec.

16. The method of claim 9, wherein the first and second laser beams are transmitted simultaneously towards different target areas of the duodenal wall.

17. The method of claim 9, further comprising rotating a deflective optical element, such that said first and/or second laser beam are deflected toward the duodenal wall in an essentially circumferential pattern.

18. The method of claim 9, wherein evaluating the extent of impact on the region of the duodenal wall comprises determining the depth and/or width of the ablative damage.

19. The method of claim 9, further comprising adjusting parameters related to the first laser beam, based on the evaluated extent of impact on the region of the duodenal wall detected by the second laser beam.

* * * * *